United States Patent [19]

Kleiner et al.

[11] Patent Number: 4,960,919
[45] Date of Patent: Oct. 2, 1990

[54] PROCESS FOR THE PREPARATION OF ALKYL ALKENYLPHOSPHINATES

[75] Inventors: Hans-Jerg Kleiner, Kronberg/Taunus; Günter Roscher, Kelkheim, both of Fed. Rep. of Germany

[73] Assignee: Hoechst Aktiengesellschaft, Frankfurt, Fed. Rep. of Germany

[21] Appl. No.: 311,527

[22] Filed: Feb. 16, 1989

[30] Foreign Application Priority Data

Feb. 19, 1988 [DE] Fed. Rep. of Germany ....... 3805205

[51] Int. Cl.⁵ .............................................. C07F 9/40
[52] U.S. Cl. .................................... 558/142; 558/207
[58] Field of Search ............................... 558/142, 207

[56] References Cited

FOREIGN PATENT DOCUMENTS 281122 9/1988 European Pat. Off. ............. 558/142
455116 5/1975 U.S.S.R. ................................ 558/207

OTHER PUBLICATIONS

Kabachnik et al., "Chem. Abstracts", vol. 58, (1963) #9126g.
Kamai et al., "Chem. Abstracts", vol. 54, (1960) #7538g.

*Primary Examiner*—Mukund J. Shah
*Assistant Examiner*—C. L. Cseh

[57] ABSTRACT

A process for the preparation of alkyl esters of alkenylphosphinic acid, having the general formula I

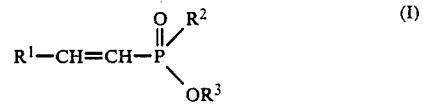

wherein $R^1$ represents H or $CH_3$, $R^2$ alkyl having from 1 to 4 carbon atoms or phenyl and $R^3$ alkyl having from 1 to 8 carbon atoms, which comprises cleaving an alkyl ester of 2-acetoxyethyl phosphinic acid, having the general formula II

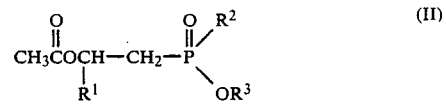

wherein $R^1$, $R^2$ and $R^3$ have the meaning indicated above, in contact with a liquid catalytically acting medium and at a partial pressure of the total of the components of the reaction system in the range of from 1 to 500 mbar, and drawing off the resulting alkyl esters of alkenyl phosphinic acid and other volatile reaction products.

The invention also relates to compounds of the formula I

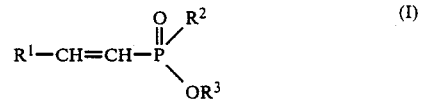

wherein
(a) $R^1$ represents H, $R^2$ represents alkyl having from 1 to 4 carbon atoms or phenyl and $R^3$ represents isobutyl or alkyl having from 5 to 8 carbon atoms, or
(b) $R^1$ represents $CH_3$, $R^2$ represents alkyl having from 1 to 4 carbon atoms or phenyl and $R^3$ represents alkyl having from 1 to 8 carbon atoms.

20 Claims, No Drawings

PROCESS FOR THE PREPARATION OF ALKYL ALKENYLPHOSPHINATES

The invention relates to a process for the preparation of alkyl alkenylphosphinates.

Alkenylphosphinic acid esters are valuable intermediate products. For example, alkyl alkenylalkylphosphinates have been reacted with 2,5-dialkoxy-3,6-dihydro-1,4-pyrazines and substantially pure enantiomers of (3-amino-3-carboxy-propyl)-alkylphosphinic acid derivatives have been obtained in this reaction (German Offenlegungsschrift 3,525,267). The hydrolysis of methylvinylphosphinic acid esters also gives methylvinylphosphinic acid. Polymerization of the latter results in polyvinylmethylphosphinic acid, which has valuable properties for industry as a water-soluble, acidic polymer. Thus it is, for example, an excellent agent for the treatment of support materials for offset printing plates (European Published Specification 69,318 = U.S. Pat. 4,458,005).

Various processes for preparing vinylphosphinic acid esters have been disclosed hitherto. For example, it is possible to react phosphonic acid ester-chlorides in tetrahydrofuran as solvent with vinyl magnesium chloride. The vinylphosphinic acid esters are obtained in this way; for example, methyl methylvinylphosphinate is obtained by this process in a yield of 61% of theory [N. Minowa et al., Tetrahedron Letters 24, 2391 (1983)]. A process which can easily be carried out industrially continues, however, to be very desirable, since the processes at the present time can only be carried out with difficulty on an industrial scale.

It has now been found, surprisingly, that alkenylphosphinic acid esters of the general formula I

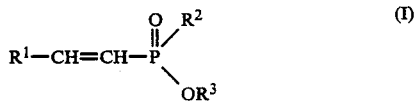

(I)

in which $R^1$ denotes $CH_3$, or preferably H, $R^2$ denotes phenyl or alkyl having 1 to 4, preferably 1 or 2, carbon atoms, particularly methyl, and $R^3$ denotes alkyl having 1 to 8 carbon atoms, can be prepared by splitting alkyl 2-acetoxyethylphosphinates corresponding to the general formula II

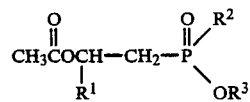

(II)

in which $R^1$, $R^2$ and $R^3$ have the meaning indicated above, under a partial pressure of the sum of the components of the reaction system between 1 and 500 mbar, preferably between 5 and 100 mbar, in contact with a liquid, catalytically active medium, and removing, in the form of vapor, the resulting alkyl alkenylphosphinates of the formula I and other volatile reaction products.

It was already known to convert dialkyl 2-acetoxyethanephosphonates, by the process of German Offenlegungsschrift 3,001,894 = U.S. Pat. No. 4,388,252 in the presence of acid or basic catalysts, at 150°–270° C. under atmospheric pressure, with the elimination of alkyl acetates, into mixtures of vinylphosphonic acid derivatives which, in addition to monoalkyl vinylphosphonates and several other products, also contain small quantities (23% at the most) of dialkyl vinylphosphonates.

Accordingly, only a low yield of the desired alkyl alkenylphosphinates would also be expected in the analogous pyrolysis of the alkyl 2-acetoxyethylphosphinates of the formula II.

Surprisingly, however, the main product formed, with the elimination of acetic acid instead of acetic acid esters, is an alkenylphosphinic acid ester of the formula I, i.e. a vinylphosphinic acid ester if $R^1$ is H.

The 2-acetoxyethylphosphinic acid esters of the general formula II which are used as starting materials are readily accessible by known processes. In particular, they can be prepared by the process of German Patent No. 2,127,821, in which vinyl acetate or isopropenyl acetate is added on to phosphonous acid monoesters by free-radical catalysis.

Although the present process is in practice particularly suitable for the preparation of esters having alkyl groups of 1 to 4 carbon atoms, such as the methyl, ethyl, propyl, isopropyl and the various butyl esters, it is also possible to prepare esters having alkyl groups of more than 4 carbon atoms, such as those having the various pentyl, hexyl, heptyl and octyl groups. In general, the esters prepared in accordance with the invention thus contain alkyl groups having not more than 8, preferably not more than 5, carbon atoms. The following starting materials may be mentioned as examples: methyl, ethyl, n-butyl, isobutyl, pentyl, isopentyl and hexyl 2-acetoxyethylmethylphosphinates; methyl, ethyl and n-butyl 2-acetoxyethylethylphosphinates; methyl, ethyl, n-butyl and isobutyl (2-acetoxy-2-methyl-ethyl)-methylphosphinates; and methyl, ethyl and n-butyl 2-acetoxyethylphenylphosphinates. Thus the following are then obtained from these: methyl, ethyl, n-butyl, isobutyl, pentyl, isopentyl and hexyl methylvinylphosphinates; methyl, ethyl and n-butyl ethylvinylphosphinates; methyl, ethyl, n-butyl and isobutyl (methylvinyl)-methylphospinates; and methyl, ethyl and n-butyl phenylvinylphosphinates.

Compounds of the formula I in which $R^1$ is methyl and also such compounds in which $R^1$ is hydrogen, $R^2$ has the meaning indicated above and $R^3$ denotes isobutyl or alkyl having 5 to 8 carbon atoms, are novel and also form a subject-matter of the present invention.

The process according to the invention is generally carried out at a temperature of 150° to 270°, preferably of 180° to 250° C.

The expression "partial pressure of the sum of the components in the reaction system" embraces both the pressure of the alkyl 2-acetoxyethylphosphinate of the formula II and that of the reaction products formed therefrom, which are for the most part more volatile than the starting material and in this respect can be removed from the mixture by distillation. The pressure mentioned, for example between 10 and 100 mbar, can be obtained in various ways. In one embodiment, the reaction is carried out under reduced pressure; in another procedure, the reaction is carried out under a pressure of more than 500 mbar, it being possible to produce the difference between the total pressure and the desired partial pressure of the components in the reaction system by means of a gas which is inert towards the reactants under the conditions of the reaction. In this embodiment it is advantageous for the total pressure in the reaction system to be 5 to 500 mbar. Suitable inert gases of this type are those which are customary in practice, above all nitrogen, but also, if appropriate, carbon dioxide or light hydrocarbons, such as methane or ethane, and, in special cases, also noble gases, such as argon. It is, of course, also possible to use mixtures of various gases of this type.

Suitable media having a catalytic action are the same as those mentioned in German Offenlegungsschrift 3,001,894, specifically either acid or basic media. Examples of suitable acid media are sulfuric acid, phosphoric acid, halogen-containing carboxylic acids, such as dichloroacetic and trichloroacetic acids and also trifluoroacetic acid, aromatic sulfonic acids, such as benzenesulfonic and p-toluenesulfonic acids, vinylphosphonic acid and alkenylphosphinic acids, but, above all, products which are obtained from the byproducts formed as a bottom product in the present reaction, i.e. higher-boiling byproducts, by heating the latter with water, it being possible to carry out the treatment with water by, for example, boiling for a period of 5 minutes to 2 hours. Examples of basic media which can be used are tertiary aliphatic and aromatic amines and phosphanes (previously described as phosphines), such as are also mentioned in large numbers in German Offenlegungsschrift 3,001,894.

The medium having a catalytic action is generally used in an amount of at least 0.1% by weight, relative to the alkyl acetoxyethylphosphinate put through. The concentration in the reaction mixture is, naturally, substantially higher, since its acts as the reaction medium. In general, its amount is 1-20% by weight, it being, of course, preferable to use the smallest possible amounts, advantageously not more than 5% by weight, relative to the alkyl acetoxyethylphosphinate put through. On the other hand, and this applies above all when using the byproducts of the reaction according to the invention which have been treated with water, it is also possible to use the media having a catalytic action in amounts even larger than 20% by weight without endangering the feasibility of the reaction. The term % by weight relates in every case to the weight of alkyl acetoxyethylphosphinate.

The process according to the invention can be carried out discontinuously, but also, with particular advantage, continuously, the cleavage products formed, especially the alkyl alkenylphosphinate, being removed continuously from the reaction mixture by distillation.

If desired, the alkyl alkenylphosphinates prepared in accordance with the invention can also be purified further by distillation.

The invention is illustrated by means of the following examples.

EXAMPLES:

(1) The experimental set-up comprised a 0.5 liter stirred flask equipped with a dropping funnel and a glass column mounted on the flask having a vacuum jacket (internal diameter 29 mm, length 0.5 m, packed with 6 mm Raschig rings), an automatic reflux divider, a condenser, a cold trap, a receiver and a vacuum pump.

100 g of methylvinylphosphinic acid were initially placed in the stirred flask as catalyst for the cleavage reaction. The sump was heated with stirring to 200° C., under a pressure of 10 mbar. 70 g per hour of ethyl 2-acetoxyethylmethylphosphinate were then added dropwise from the dropping funnel. 58 g per hour of condensate were obtained in all as distillate and in the cold trap at a reflux ratio of 1 and a head temperature of 95°-102° C. in the column. The mixture contained 64% by weight of ethyl methylvinylphosphinate and 25% of acetic acid; the remainder consisted of other phosphinic acid derivatives and unknown components. Calculation gave the yield of methylvinylphosphinic acid ester as 76%.

(2) Vinylphosphonic acid was initially placed, as catalyst for the cleavage reaction, in the experimental apparatus described in example 1. The sump was heated with stirring to 205°-210° C. under a pressure of approx. 10-15 mbar. Isobutyl 2-acetoxyethylmethylphosphinate, in which a few percent of vinylphosphonic acid had been admixed, was then added dropwise. A distillate and a bottom product were obtained at a reflux ratio of approx. 1 and a head temperature of 55°-64° C. The distillate consisted mainly of isobutyl vinylmethylphosphinate which, after further purification, was obtained with a boiling point of 43° C./0.15 mbar and 1.4435.

(3) If the procedure was analogous to that of Example 1 and a mixture of amyl esters of 2-acetoxyethylmethylphosphinate (amyl component n-pentyl and 2-methylbutyl) was used as the starting material, an ester mixture was obtained which contained 80% of the n-pentyl component and about 20% of the 2-methylbutyl component. Characteristics: bp 75° C./0.4 mbar, $n_D^{20} = 1.4470$.

We claim:

1. A process for the preparation of alkyl esters of alkenylphosphinic acid, having the general formula I

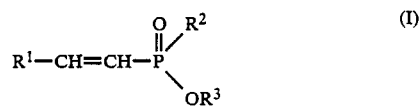

wherein $R^1$ represents H or $CH_3$, $R^2$ represents alkyl having from 1 to 4 carbon atoms or phenyl and $R^3$ represents alkyl having from 1 to 8 carbon atoms, which comprises cleaving an alkyl ester of 2-acetoxyethyl phosphinic acid, having the general formula II

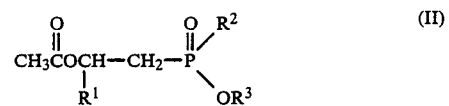

wherein $R^1$, $R^2$ and $R^3$ have the meaning indicated above, in contact with a liquid, catalytically acting medium and at a partial pressure of the total of the components of the reaction system in the range of from 1 to 500 mbar, and drawing off the resulting alkyl esters of alkenyl phosphinic acid and other volatile reaction products.

2. A process as claimed in claim 1, wherein the cleavage is carried out a total pressure above 500 mbar with the proviso that the differential pressure between the total pressure and the partial pressure of the total of the components of the reaction system results from a gas inert towards the components of the reaction system under the reaction conditions.

3. A process as claimed in claim 1, wherein the total pressure is adjusted in the reaction system to a range of from 1 to 500 mbar.

4. A process as claimed in claim 1, wherein the partial pressure of the total of the components of the reaction system is in the range of from 5 to 100 mbar.

5. A process as claimed in claim 2, wherein the inert gas is nitrogen, carbon dioxide, methane, ethane or a noble gas.

6. A process as claimed in claim 1, wherein the temperature is in the range of from 150° to 270° C.

7. A process as claimed in claim 6, wherein the temperature is in the range of from 180° to 250° C.

8. A process as claimed in claim 1, wherein $R^3$ is alkyl having from 1 to 5 carbon atoms.

9. A process as claimed in claim 1, wherein $R^3$ is alkyl having from 1 to 4 carbon atoms.

10. A process as claimed in claim 9, wherein $R^2$ has 1 to 2 carbon atoms.

11. A process as claimed in claim 1, wherein $R^1$ represents hydrogen.

12. A process as claimed in claim 1, wherein the catalytically acting medium is applied in an amount of at least 0.1 and at most 20 %, referred to the weight of the alkyl ester of the acetoxyethyl phosphinic acid introduced in the reaction.

13. A process as claimed in claim 12, wherein the catalytically acting medium is applied in an amount of at least 1 %.

14. A process as claimed in claim 13, wherein the catalytically acting medium is applied in an amount in the range of from 1 to 5 %.

15. A process as claimed in claim 1, wherein an acidic catalytically acting medium is used.

16. A process as claimed in claim 15, wherein a liquid catalytically acting medium is used which has been formed in the reaction as a higher boiling by-product and subsequently has been treated in the hot with water.

17. A process as claimed in claim 16, wherein the said by-product has been treated with boiling water for 5 minutes to 2 hours.

18. A process as claimed in claim 1, wherein the cleavage products formed are continuously removed from the reaction zone.

19. A process for the preparation of alkyl esters of alkenylphosphinic acid, having the general formula I

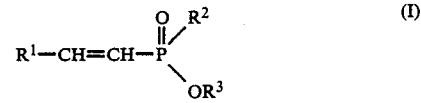

wherein $R^1$ represents H or $CH_3$, $R^2$ alkyl having from 1 to 2 carbon atoms and $R^3$ alkyl having from 1 to 5 carbon atoms, which comprises cleaving an alkyl ester of 2-acetoxyethyl phosphinic acid, having the general formula II

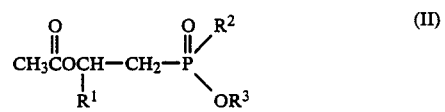

wherein $R^1$, $R^2$ and $R^3$ have the meaning indicated above, in contact with a liquid acidic catalytically acting medium at a temperature in the range of from 180 to 250° C. and under a partial pressure of the total of the components of the reaction system in the range of from 5 to 100 mbar, and drawing off the resulting alkyl esters of alkenyl phosphinic acid and other volatile reaction products.

20. A process as claimed in claim 19, wherein a liquid acidic catalytically acting medium is applied in an amount in the range of from 1 to 5 %, referred to the weight of the alkyl ester of the acetoxyethyl phosphinic acid introduced in the reaction.

* * * * *